United States Patent [19]

Moggi et al.

[11] 4,046,810

[45] Sept. 6, 1977

[54] PROCESS FOR THE PREPARATION OF DIPHENYLAMINE AND DERIVATIVES THEREOF

[75] Inventors: Pietro Antonio Moggi; Ugo Romano, both of Milan, Italy

[73] Assignee: SNAM Progetti S.p.A., San Donato Milanese, Italy

[21] Appl. No.: 552,296

[22] Filed: Feb. 24, 1975

Related U.S. Application Data

[63] Continuation of Ser. No. 369,494, June 13, 1973, abandoned.

[30] Foreign Application Priority Data

June 24, 1972 Italy .................................. 26169/72

[51] Int. Cl.² ..................... C07C 87/54; C07C 91/16; C07C 91/18
[52] U.S. Cl. ................................. 260/571; 252/455 R; 252/456; 252/458; 252/464; 252/465; 260/576
[58] Field of Search ............................ 260/576, 571

[56] References Cited

U.S. PATENT DOCUMENTS

| | | | |
|---|---|---|---|
| 2,413,598 | 12/1946 | Ballard et al. | 260/576 X |
| 3,219,702 | 11/1965 | Van Verth et al. | 260/571 |
| 3,219,704 | 11/1965 | Wilder et al. | 260/576 |
| 3,953,508 | 4/1976 | Kalopissis et al. | 260/571 |

OTHER PUBLICATIONS

Morrison et al., "Organic Chemistry", 3rd Edition, pp. 740 and 741, (1974).

*Primary Examiner*—Daniel E. Wyman
*Assistant Examiner*—John J. Doll
*Attorney, Agent, or Firm*—Morgan, Finnegan, Pine, Foley & Lee

[57] ABSTRACT

Diphenylamine, or the alkyl, phenyl, amino, alkoxy, hydroxy or halogen derivative thereof, is prepared through a continuous process wherein a stream of the corresponding imine (e.g. N-cyclohexylidene aniline) in the vapor phase and oxygen are fed to a reactor maintained at a temperature in the range from 300° to 450° C, at a rate providing a contact time between the reactants in the range of 0.1 to 20 seconds.

9 Claims, No Drawings

PROCESS FOR THE PREPARATION OF DIPHENYLAMINE AND DERIVATIVES THEREOF

This is a continuation of application Ser. No. 369,494, filed June 13, 1973, now abandoned.

The present invention relates to a process for the production of diphenylamine and derivatives thereof starting from imines of the type represented by the following formula

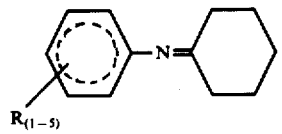

wherein R is a substituent selected from the group consisting of alkyl, H, phenyl, amine, alkoxy, hydroxy and halogen.

Such imines may be easily synthesized according to methods described in scientific papers, for instance starting from aromatic amines (particularly aniline and derivatives thereof containing substituents in the benzene ring) and cyclohexanone.

We have now found, which is the subject of the present invention, that it is possible to obtain diphenylamine and substituted derivatives thereof by reacting, in the vapour phase, N-cyclohexilidene aniline and derivatives thereof with molecular oxygen or oxygen containing gas, which is preferably constituted by air.

The reaction is carried out at high temperature and may be performed in the presence of an inert diluent such as nitrogen, argon, carbon dioxide, steam, benzene and saturated hydrocarbons stable under the reaction conditions.

The molar ratio between oxygen and imine in the feed depends on the imine structure; it may range from 0.2 : 1 to 20 : 1, and preferably from 0.8 : 1 to 10 : 1.

The reaction may be carried out in the absence of any contact material, or use may be made of suitable catalysts.

Illustrative examples of employable contact materials are the ones usually employed as oxidation catalysts such as silica, alumina, silica-alumina, silica-aluminates, oxides or oxide mixtures, or compounds of metals belonging to groups III-VIII of the periodic system.

A procedure preferably followed in performing the inventive process consists in reacting an imine with molecular oxygen or oxygen containing gas in the vapour phase, at a temperature in the range from 300° to 450° C on a contact material, fundamentally constituted by active silica.

The reaction can be carried out in any type of reactor, i.e. of fixed, moving or fluid bed type.

A temperature range particularly preferred is the one from 400° to 450° C; the pressure may range from a few millimeters of mercury to 10 atmospheres, but it is preferable to work at the atmospheric pressure.

The apparent contact time between reagents and catalyst is selected from the range between 0.1 and 20 seconds, particularly between 0.5 and 10 seconds. By contact time we mean the ratio between the reactor volume wherein the reaction occurs and the flow of the reagents in the gaseous state under the reaction conditions.

The invention will be better understood by examining the following examples, which are not to be interpreted as limitative thereof, but when only purpose is to illustrate some possible practices of the inventive process in preparing diphenylamine and derivatives thereof having an industrial interest.

In the examples, the terms conversion, selectivity and yield terms are to be understood as follows:

$$\text{conversion} = \frac{\text{reacted imine moles}}{\text{fed imine moles}} \cdot 100$$

$$\text{sel.} = \frac{\text{obtained diphenylamine (or derivatives) moles}}{\text{reacted imine moles}} \cdot 100$$

$$\text{yield} = \frac{\text{obtained diphenylamine (or derivatives) moles}}{\text{fed imine moles}} \cdot 100$$

EXAMPLE 1

In a reactor having a 37.8 mm internal diameter we charged 600 cc of a catalyst constituted by silica obtained from a colloidal silica gel, at 30% of $SiO_2$ stabilized with $NH_3$ (Silica Ludox AS), by means of an atomization and extrusion into 4 mm diameter cylinder tablets, which were then calcined at 500° C.

To the reactor we fed N-cyclohexylidene aniline, air and water at a ratio of 1/30/60 at 420° C, and a contact time of 5 seconds. We obtained a conversion of imine of 38%, at a selectivity to diphenylamine of 65%.

EXAMPLE 2

600 cc of a catalyst constituted by PT (0.7%) on silica were charged in the same reactor. N-cyclohexylidene-aniline, air and water, at a ratio 1/7/20, were fed to the reactor at 450° C and a contact time of 2 seconds. An imine conversion was obtained equal to 43%, and a selectivity to diphenylamine of 50%.

EXAMPLE 3

600 cc of a catalyst constituted by celite were charged in the same reactor. N-cyclohexylidene p. toluidine, air and water at a ratio of 1/10/50 were fed to the reactor at 430° C for a contact time of 2.5 seconds.

A 43% conversion was obtained with a selectivity to 4-methyl diphenylamine equal to 61%.

EXAMPLE 4

Use was made of the same reactor and the same catalyst as example 3: thereto were sent N-cyclohexylidene P-chloroaniline, air and water in a ratio of 1/10/50, at 410° C and 5 seconds as contact time.

4-chloro-diphenyl-amine was obtained at 63% selectivity and imine conversion of 29%.

EXAMPLE 5

N-cyclohexylidene P-methoxy-aniline, air and water were fed to the same reactor and same catalyst as of example 3, in a ratio of 1/8/30 at 420° C and 3 seconds as contact time.

4-methoxy-diphenylamine was obtained at 58% selectivity and imine conversion of 35%.

EXAMPLE 6

Use was made of the same reactor, charged with 600 cc of a catalyst having the composition: 0.6 $V_2O_5$ . 1 $Bi_2O_3$ . 1.6 $MoO_3$ on 15% of silica as catalyst carrier: thereto were fed N-cyclohexylidene-aniline, air and water in a ratio of 1/7/50 and contact time of 2 seconds, at 450° C.

Diphenylamine was obtained at 46% selectivity and imine conversion of 48%.

We claim:

1. Process for the production of a member of the group consisting of diphenylamine and the alkyl, phenyl, amino, alkoxy, hydroxy and halogen derivatives thereof consisting in reacting an imine having the formula

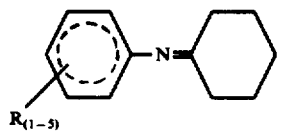

wherein R is a substituent selected from alkyl, H, phenyl, amine, alkoxy, hydroxy and halogen with oxygen at a temperature in the range from 300° C to 450° C by feeding to a reactor charged with a contact mass selected from silica, alumina, silica-alumina, silica-aluminate and oxides, oxide mixtures, and compounds of metals selected from the group consisting of V, Bi and Mo and maintained at said temperature a stream of said imine in the vapor phase, together with oxygen at a molar ratio in the range from 0.1:1 to 20:1 and at a rate providing a contact time in said reactor in the range from 0.1 to 20 seconds.

2. Process according to claim 1, wherein said molar ratio between oxygen and imine is in the range 0.8 : 1 to 10 : 1.

3. Process according to claim 1, wherein said stream fed to the reactor includes an inert diluent selected from nitrogen, argon, carbon dioxide, steam, benzene and a saturated hydrocarbon stable under the reaction conditions.

4. Process according to claim 1, wherein the reaction is carried out at a pressure ranging from a few millimeters of mercury to 10 atmospheres.

5. Process according to claim 1, wherein the reaction is carried out at a contact time in the range from 0.5 to 10 seconds.

6. Process according to claim 1, wherein the imine is N-cyclohexylidene aniline.

7. Process according to claim 1, wherein the imine is N-cyclohexylidene p. toluidene.

8. Process according to claim 1, wherein the imine is N-cyclohexylidene p-chloroaniline.

9. Process according to claim 1, wherein the imine is N-cyclohexylidene p-methoxy-aniline.

* * * * *